United States Patent [19]

Bridges

[11] Patent Number: Plant 7,738

[45] Date of Patent: Dec. 10, 1991

[54] MINIATURE ROSE NAMED 'BRISUZY'

[76] Inventor: Dennis A. Bridges, 2734 Toney Rd., Lawndale, N.C. 28090

[21] Appl. No.: 584,334

[22] Filed: Sep. 17, 1990

[51] Int. Cl.[5] ..... A01H 5/00
[52] U.S. Cl. ..... Plt./9
[58] Field of Search ..... Plt./9

[56] References Cited

U.S. PATENT DOCUMENTS

P.P. 5,097 9/1983 Saville ..... Plt. 9
P.P. 5,691 3/1986 Saville ..... Plt. 9
P.P. 7,454 2/1991 Williams ..... Plt. 9

*Primary Examiner*—James R. Feyrer

[57] ABSTRACT

A new and distinct variety of miniature rose plant characterized by a profusion of bright pink buds and blooms with a slightly lighter reverse and a vigorous, compact, highly disease resistant plant with semi-glossy foliage.

1 Drawing Sheet

FIELD OF THE INVENTION

This application is drawn to a new and novel miniature rose plant which has been assigned an international recognition name of "Brisuzy" and which will be marketed in the United States of America under the commercial synonym "Suzy".

PLANTS RELATED TO THE INVENTION

The new rose plant is of the miniature rose class, and was originated in a planned breeding program, the aim of which was to expand the range of exceptional plants available in this market class. The seed patent of the new plant was the rose variety "Party Girl", also of the miniature rose class. While the pollen parent plant of "Brisuzy" is not known with certitude, it was one of a number of selected miniature varieties from which pollen had been taken for crossing with "Party Girl" in the hope of attaining a new plant having some of the better traits of the seed parent and any one of the pollen parents plants involved in the program. The plant of this disclosure is a selection from the progeny of the stated cross(es), and has been asexually reproduced by the taking and rooting of cuttings. Clones developed in this manner through succeeding propagations are identical to the parent plant in all distinguishing characteristics and establish that "Brisuzy", is stable.

SUMMARY OF THE INVENTION

The exceptional characteristics possessed by this new variety which distinguish it from its parents and all other varieties of which I am aware are:

(1) well formed bright pink blooms of unusually strong substance.

(2) abundant blooms borne singly and in clusters of up to 7 blooms.

(3) a slight to moderately strong fruity fragrance.

(4) a plant with abundant semi glossy dark green foliage to show off the exhibition quality bright pink blooms.

(5) a very disease resistant, vigorous, compact plant, that grows well in the greenhouse or outdoors. Excellent garden display as well as an outstanding cut flower producer.

DESCRIPTION OF THE DRAWING

The accompanying drawing shows typical specimens of flowers of the new variety in different stages of maturity in color as accurate as is reasonably possible in color illustrations of this character.

The following is a detailed description of my new rose variety, with color terminology in accordance with The Royal Horticultural Society Colour Chart (RHSCC) except where common dictionary terms of color definition are employed.

Type: Hardy dwarf, bushy, compact, seedling, greenhouse, outdoors, cut flowers, garden decoration, potted plant.
Commercial class: Miniature Rose.
International recognition name: "Brisuzy".
Commercial Synonym: "Suzy".

FLOWER

Observations were made from specimens grown outdoors at Cleveland County, N.C. U.S.A., in June 1990

Type: Miniature.
Blooming Habit: Continuous.
Bud:
*Size.*—Medium for a miniature.
*Form.*—Urn shaped.
*Color.*—When sepals first divide.—Medium pink (48-C). When petals begin to unfurl.—Medium pink (48-C). When half-Blown.—Medium pink (48-C). Reverse side of petals.—White base (19-C) blending to light pin (49-A). Sepals: As long as the bud light green with a little reddish fuss.
*Peduncle.*—One inch in length, strong, erect, green (C143) with reddish tips.
Bloom:
*Size.*—1½ inches when fully expanded.
*Borne.*—Singly and in sprays of up to 7 blooms.
*Form.*—Symmetrical, high centered, opening with reflexing petals, becoming flat with age.
*Petalage.*—42 under normal conditions.
*Color.*—During first two days: Inner petals at center of flower: Bright pink (48-C). Outer petals:

Bright pink (48-C). Base of petals (point of attachment): Creamy white (19-C). Reverse of petals: Off white at base (19-D), blending to light pink (49-A). General tonality from a distance: Bright pink (48-D).

Color change: As bloom ages pink lightens slightly (48-D).

*General tonality.*—Bright pink (48-D).

*After three or more days.*—Bright pink (48-D) with edges of petals showing a slightly deeper pink (48-C).

Petals:

*Texture.*—Thick, ½ inch in length.

*Appearance.*—Velvety inside, satiny outside.

*Form.*—Round, quilling on edges causing petals to point.

*Arrangement.*—Regular.

*Petaloids in center.*—Few.

*Persistence.*—Drop off cleanly after extensive time on bush.

*Fragrance.*—Light fruity fragrance.

*Lasting quality.*—Blooms last a long time on plant (5 to 7 Days). Longer lasting as a cut flower.

REPRODUCTIVE ORGANS

Stamens, filaments and anthers:

*Arrangement.*—Regularly arranged around styles.

*Color.*—Yellow.

Pollen: Yellow.

Styles: Uneven Length, Bunches, Thin.

Stigmas:

Color.—Pale Green.

Hips:

*Shape.*—Globular.

*Size.*—½ inch in diameter.

*Color.*—Orange when mature.

*Seeds.*—A few seeds do protrude.

PLANT

Form: Upright, compact growth.

Growth: Vigorous, uniform branching, bushy full plant approximately 10 main canes, slightly spreading, producing numerous flower stems.

Foliage: Combination of 5 to 7 leaflets.

*Size.*—Medium—Each leaf in a leaflet is 2 to 3 cm.

*Height attained.*—18 to 22 inches at maturity upon maturity plant is approximately 2 feet across.

*Quantity.*—Abundant.

*Color.*—New foliage: Upper side: glossy green near to A137, red edges. Under side: lighter green near to D137, with red overtones. Old foliage: Upper side: semi glossy dark green near to A137. Under side: Lighter green near to B138.

*Shape.*—Oval with pointed tips.

*Texture.*—Upper side: smooth. Under side: raised veins.

*Edge.*—Serrated.

*Serration.*—Irregular indentations.

*Leaf stem.*—Color: Green. Under side: Paler green.

*Stipules.*—½ inch in length and pointed.

*Disease resistance.*—Blackspot, good; mildew, good; rust, good.

Wood:

*New wood.*—Medium green near to B143.

*Old wood*—Darker green near to A143.

Thorns:

*Quantity.*—Few on main canes.

*Form.*—Sharp, straight with oval base.

*Length.*—¼ to ⅜ inches long.

*Color when young.*—Near to B151 at base. Near to A151 at tip.

*Position*: Irregular.

Prickles:

*Quantity.*—No moss on canes or laterals.

Winter hardiness: Very winter hardy with little or no die back.

*Lows.*—Average winter temp. low teens to an occasional—degree temp.

I claim:

1. A new and distinct variety of rose plant of the miniature rose class, substantially as herein shown and described, characterized particularly by an abundance of bright pink blooms of unusually strong substance, firm, thick petals, borne singly and in sprays, on a compact plant with semi-glossy dark green foliage, said plant being easy to propagate from cuttings, and said blooms being long lasting both on the plant and as cut flowers.

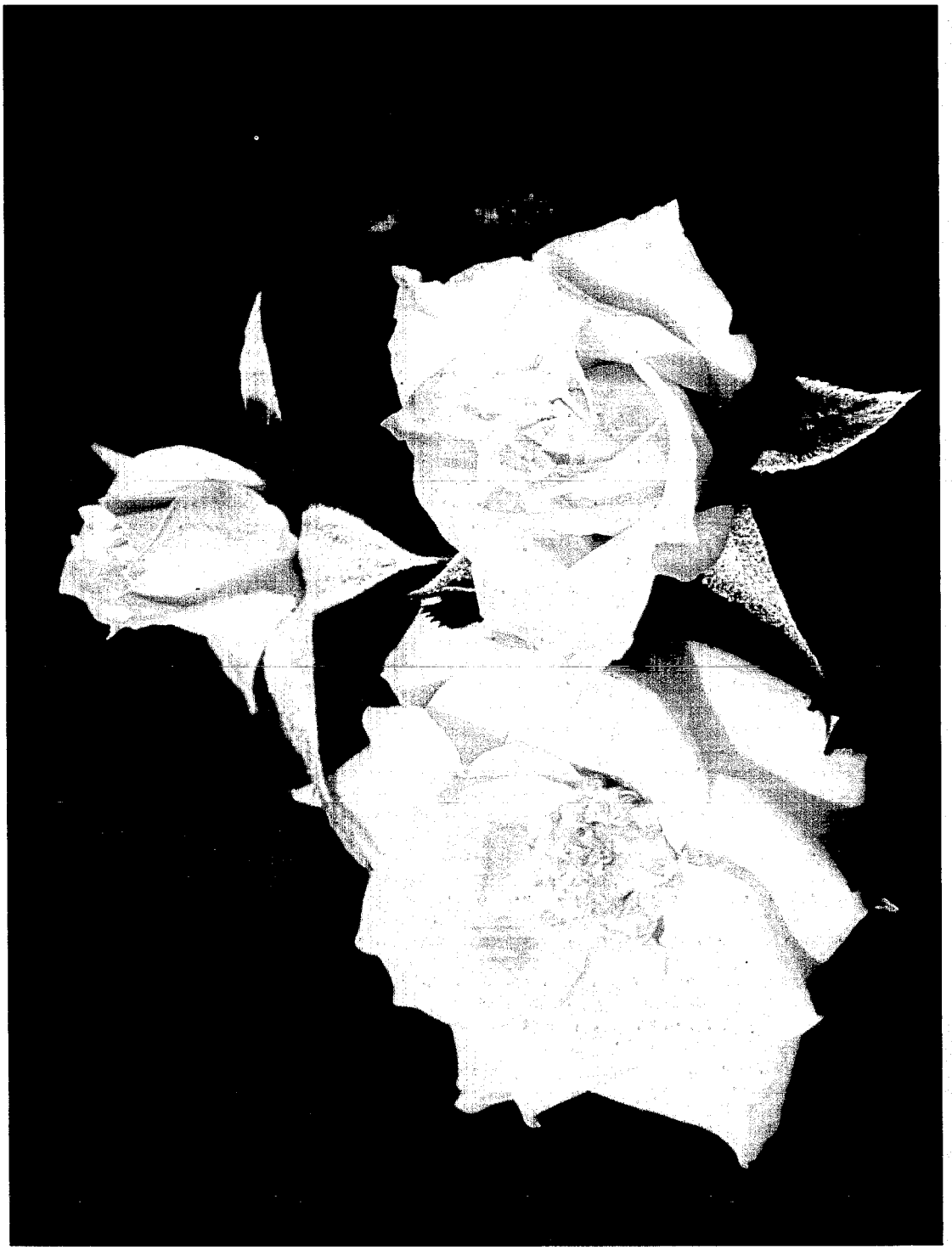

* * * * *